US012648937B2

(12) United States Patent
Li et al.

(10) Patent No.: US 12,648,937 B2
(45) Date of Patent: Jun. 9, 2026

(54) COMPOSITION CONTAINING LEVAMLODIPINE BESYLATE HYDRATE AND ITS PREPARATION METHOD

(71) Applicants:SHIHUIDA PHARMACEUTICALS GROUP (JILIN) LTD., Baishan (CN); BEIJING WUWEI ERCHUANG TECHNOLOGY CO., LTD., Beijing (CN)

(72) Inventors: Huan Li, Shanghai (CN); Fuqing Yao, Beijing (CN); Xitian Zhang, Changchun (CN)

(73) Assignees: SHIHUIDA PHARMACEUTICALS GROUP (JILIN) LTD., Baishan (CN); BEIJING WUWEI ERCHUANG TECHNOLOGY CO., LTD., Beijing (CN)

( * ) Notice: Subject to any disclaimer, the term of this patent is extended or adjusted under 35 U.S.C. 154(b) by 1070 days.

(21) Appl. No.: 17/774,922

(22) PCT Filed: Oct. 26, 2020

(86) PCT No.: PCT/CN2020/123670
§ 371 (c)(1),
(2) Date: May 6, 2022

(87) PCT Pub. No.: WO2021/088672
PCT Pub. Date: May 14, 2021

(65) Prior Publication Data
US 2022/0401427 A1 Dec. 22, 2022

(30) Foreign Application Priority Data

Nov. 8, 2019 (CN) .......................... 201911137739.6

(51) Int. Cl.
| | |
|---|---|
| *A61K 31/4422* | (2006.01) |
| *A61K 9/00* | (2006.01) |
| *A61K 9/16* | (2006.01) |
| *A61K 47/32* | (2006.01) |
| *A61K 47/38* | (2006.01) |

(52) U.S. Cl.
CPC ........ *A61K 31/4422* (2013.01); *A61K 9/0004* (2013.01); *A61K 9/1676* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,828,339 | B2 | 12/2004 | Ettema et al. |
| 2011/0313006 | A1 | 12/2011 | Yang et al. |

FOREIGN PATENT DOCUMENTS

| | | | |
|---|---|---|---|
| CN | 1355162 | * | 6/2002 |
| CN | 1355162 | A | 6/2002 |
| CN | 1824320 | A | 8/2006 |
| CN | 101766611 | A | 7/2010 |
| CN | 102266333 | * | 12/2011 |
| CN | 105111137 | A | 12/2015 |
| CN | 107320462 | A | 11/2017 |
| CN | 110882249 | A | 3/2020 |
| CN | 110882249 | B | 4/2021 |

OTHER PUBLICATIONS

Yingjun et al. (CN 102266333; published: Dec. 7, 2011), English machine translation obtained: May 20, 2025. (Year: 2025).*
Ling et al. (CN 105111137; published: Dec. 2, 2015; in IDS dated Jul. 15, 2022), English machine translation obtained May 20, 2025. (Year: 2025).*
Zhang, CN 1355162, published: Jun. 26, 2002; English machine translation obtained on Nov. 18, 2025. (Year: 2025).*
International Search Report mailed Jan. 27, 2021 in PCT/CN2020/123670 (w/English translation).
First Chinese Office Action issued in Chinese patent application No. 201911137739.6 dated May 7, 2020, with English language translation thereof.
Second Chinese Office Action issued in Chinese patent application No. 201911137739.6 dated Sep. 28, 2020, with English language translation thereof.
First Chinese Office Action issued in Chinese patent application No. 202110353060.1 dated Dec. 9, 2021, with English language translation thereof.
Second Chinese Office Action issued in Chinese patent application No. 202110353060.1 dated Mar. 30, 2022 with English language translation thereof.
Office Action issued Jan. 26, 2023, in corresponding Russian Application No. 202291141/28 (13 pages) with an English translation (6 pages).

* cited by examiner

*Primary Examiner* — Genevieve S Alley
(74) *Attorney, Agent, or Firm* — Banner & Witcoff, Ltd.

(57) ABSTRACT

The present invention relates to a composition comprising levamlodipine besylate hydrate and its production, pharmaceutical preparations and use, especially the composition of (S)-2-[(2-aminoethoxy)methyl]-4-(2-chlorophenyl)-6-methyl-1,4-dihydro-3,5-pyridinedicarboxylic acid-3-ethyl ester, 5-methyl ester benzenesulfonic acid hydrate and its production method and use. The composition of levamlodipine besylate crystallized in pure water and dried is easy for industrial production, has no organic solvent residue, good thermal stability and good dissolution amount in solid-form preparations.

7 Claims, 8 Drawing Sheets

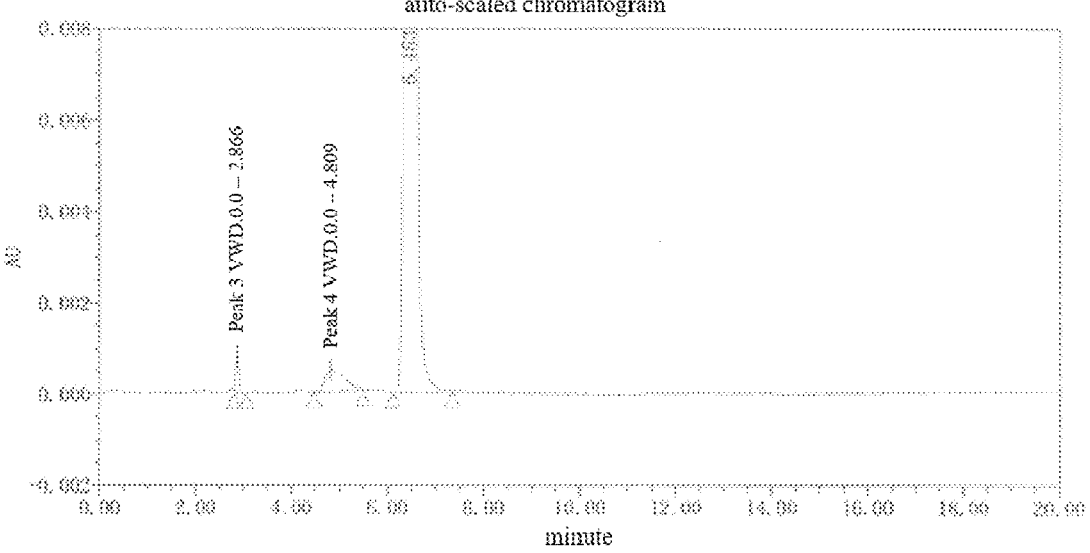

| Sample Information | | | | |
|---|---|---|---|---|
| Sample Name | 181234-3    relevant substance | Sample Collector | zhangjianye | |
| Sample Type | Unknown | Sample Group Name | active    pharmaceutical    ingredient test2018121702 | |
| Vial Number | 1:C,4 | Collecting Method Group | BHSZXALDP_HL_YGWZ_QC055a | |
| Number    of    Sample Feeding | 1 | Processing Method | levamlodipine besylate hydrate relevant substance 1 | |
| Volume of Sample | 20.00 ul | Channel Name | VWD.0.0 | |
| Operation Time | 20.0 Minutes | Processing    Channel Annotation | VWD: Signal A, 238 nm | |
| Collection Time | 18 December 2018. 5:17:22 CST | | | |
| Processing Time | 18 December 2018. 8:07:58 CST | | | | auto-scaled chromatogram

Peak Result

| | Name | Retention Time (Min) | Area (µV*S) | Height (µV) | %Area | Resolution | USP Number of Theoretical Plates |
|---|---|---|---|---|---|---|---|
| 1 | Peak    1 VWD.0.0 | 2.605 | | | | | |
| 2 | Peak    2 VWD.0.0 | 2.640 | | | | | |
| 3 | Peak    3 VWD.0.0 | 2.866 | 3948 | 830 | 0.30 | | 9373 |
| 4 | Peak    4 VWD.0.0 | 4.809 | 13819 | 479 | 1.06 | 4.3 | 580 |
| 5 | Peak    5 VWD.0.0 | 5.340 | | | | | |
| 6 | | 6.453 | 1284985 | 135386 | 98.64 | 3.2 | 10932 |

Figure 3

| Sample Information | | | |
|---|---|---|---|
| Sample Name | 181234-6          relevant substance | Sample Collector | zhangjianye |
| Sample Type | Unknown | Sample Group Name | active     pharmaceutical     ingredient test20181222 |
| Vial Number | 1:D,4 | Collecting Method Group | BHSZXALDP_HL_YGWZ_QC055a |
| Number    of    Sample Feeding | 1 | Processing Method | levamlodipine besylate hydrate relevant substance |
| Volume of Sample | 20.00 ul | Channel Name | VWD.0.0 |
| Operation Time | 20.0 Minutes | Processing          Channel Annotation | VWD: Signal A, 238 nm |
| Collection Time | 23 December 2018, 10:58:49 CST | | |
| Processing Time | 23 December 2018, 14:47:55 CST | | | auto-scaled chromatogram

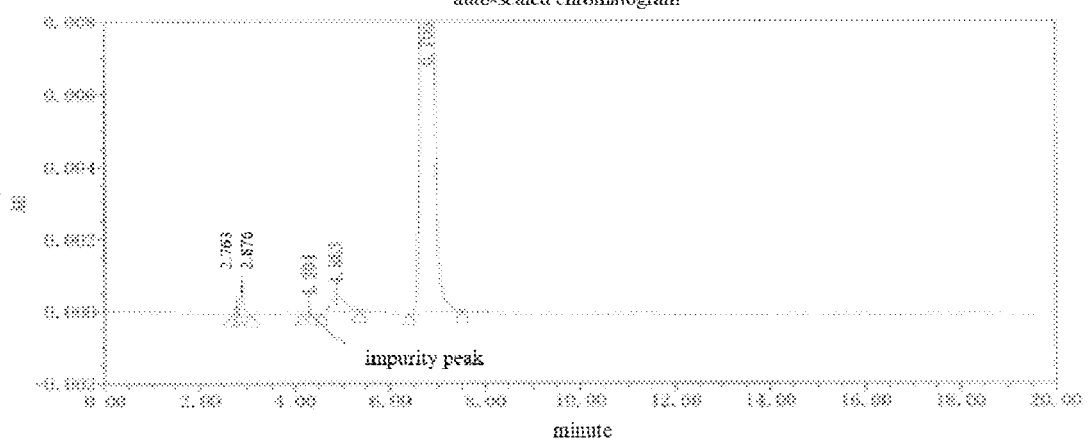

impurity peak minute

| | Name | Retention Time (Min) | Area (µV*S) | Height (µV) | %Area | Resolution | USP Number of Theoretical Plates |
|---|---|---|---|---|---|---|---|
| 1 | | 2.763 | 784 | 232 | 0.06 | | 16481 |
| 2 | | 2.876 | 3743 | 784 | 0.29 | 1.1 | 9550 |
| 3 | | 4.304 | 914 | 108 | 0.07 | 8.8 | 5423 |
| 4 | | 4.863 | 9341 | 415 | 0.72 | 1.4 | 1077 |
| 5 | | 6.765 | 1274617 | 129006 | 98.85 | 4.5 | 11053 |

Peak Result

Figure 4

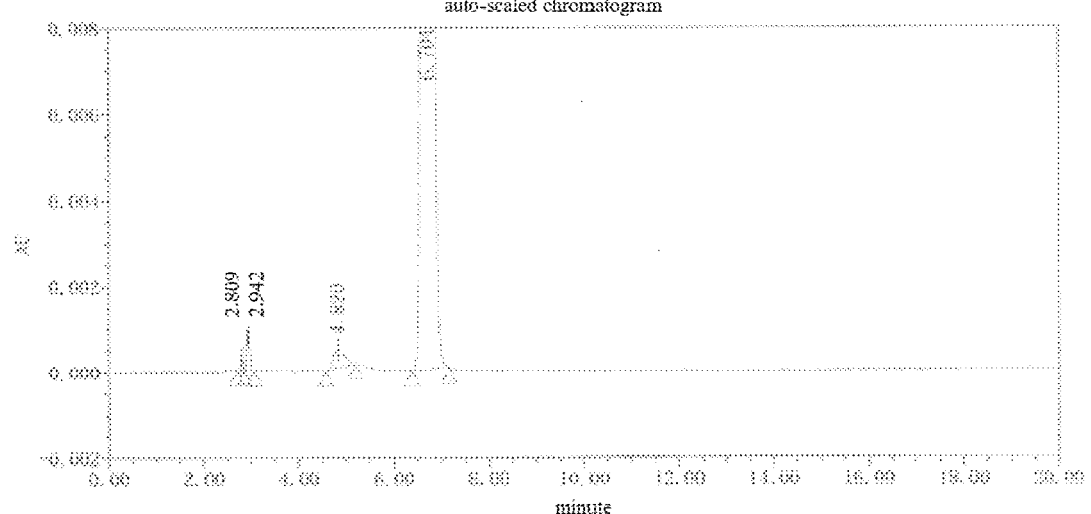

| Sample Information | | | |
|---|---|---|---|
| Sample Name | Accelerated Sample 5 | Sample Collector | fuzaisheng |
| Sample Type | Unknown | Sample Group Name | active pharmaceutical ingredient accelerated aging test20190518 |
| Vial Number | 1:A,6 | Collecting Method Group | BHSZXALDP_HL_YGWZ_QC055d |
| Number of Sample Feeding | 1 | Processing Method | levamlodipine besylate hydrate relevant substance |
| Volume of Sample | 20.00 ul | Channel Name | VWD.0.0 |
| Operation Time | 20.0 Minutes | Processing Channel Annotation | VWD: Signal A, 238 nm |
| Collection Time | 18 May 2019, 13:00:42 CST | | |
| Processing Time | 14 July 2019, 17:09:25 CST | | |

Peak Result

| | Name | Retention Time (Min) | Area (μV*S) | Height (μV) | %Area | Resolution | USP Number of Theoretical Plates |
|---|---|---|---|---|---|---|---|
| 1 | | 2.809 | 1034 | 276 | 0.08 | | 13061 |
| 2 | | 2.942 | 3567 | 792 | 0.28 | 1.2 | 9637 |
| 3 | | 4.820 | 8243 | 448 | 0.64 | 5.9 | 1342 |
| 4 | | 6.704 | 1269065 | 126492 | 99.00 | 4.9 | 10231 |

Figure 5

| Sample Information | | | |
|---|---|---|---|
| Sample Name | Accelerated Sample 5 | Sample Collector | zhangjianye |
| Sample Type | Unknown | Sample Group Name | active pharmaceutical ingredient accelerated aging test20190522 |
| Vial Number | 1:A,6 | Collecting Method Group | BHSZXALDP_HL_YGWZ_QC055d |
| Number of Sample Feeding | 1 | Processing Method | levamlodipine besylate hydrate relevant substance |
| Volume of Sample | 20.00 ul | Channel Name | VWD.0.0 |
| Operation Time | 20.0 Minutes | Processing Channel Annotation | VWD: Signal A, 238 nm |
| Collection Time | 22 May 2019, 18:24:08 CST | | |
| Processing Time | 14 July 2019, 17:14:09 CST | | | auto-scaled chromatogram

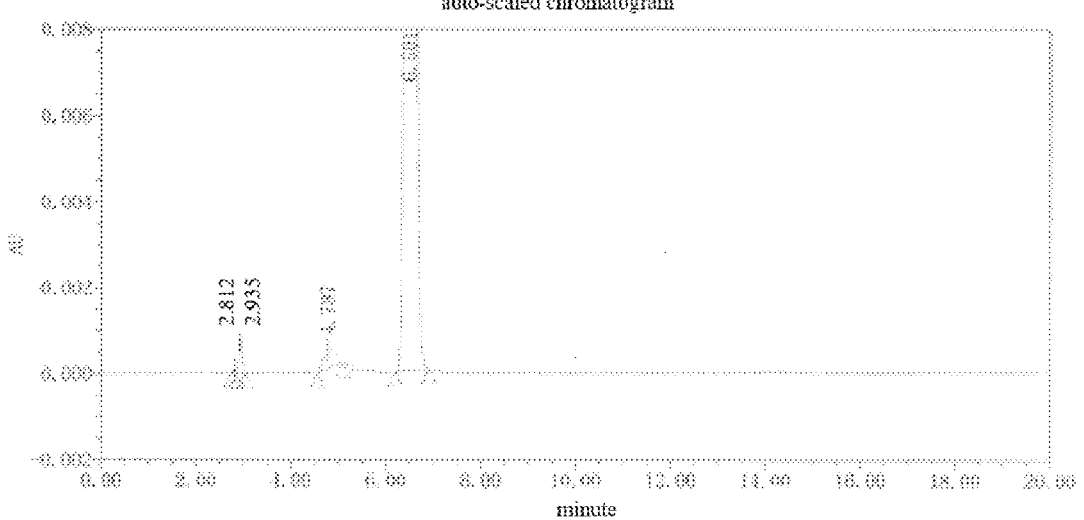

| | Name | Retention Time (Min) | Area (µV*S) | Height (µV) | %Area | Resolution | USP Number of Theoretical Plates |
|---|---|---|---|---|---|---|---|
| 1 | | 2.812 | 318 | 108 | 0.02 | | 19735 |
| 2 | | 2.935 | 3347 | 787 | 0.26 | 1.3 | 10762 |
| 3 | | 4.787 | 7005 | 427 | 0.55 | 6.3 | 1739 |
| 4 | | 6.501 | 1263676 | 137271 | 99.16 | 4.8 | 11508 |

Figure 6

| Sample Information | | | |
|---|---|---|---|
| Sample Name | 181234-2    relevant    substance | Sample Collector | zhangjianye |
| Sample Type | Unknown | Sample Group Name | active    pharmaceutical    ingredient    test2018121702 |
| Vial Number | 1:C.2 | Collecting Method Group | BHSZXALDP_HL_YGWZ_QC055a |
| Number    of    Sample    Feeding | 1 | Processing Method | levamlodipine besylate hydrate relevant    substance 1 |
| Volume of Sample | 20.00 ul | Channel Name | VWD.0.0 |
| Operation Time | 20.0 Minutes | Processing    Channel    Annotation | VWD: Signal A, 238 nm |
| Collection Time | 18 December 2018, 4:17:14 CST | | |
| Processing Time | 18 December 2018, 8:07:58 CST | | | auto-scaled chromatogram

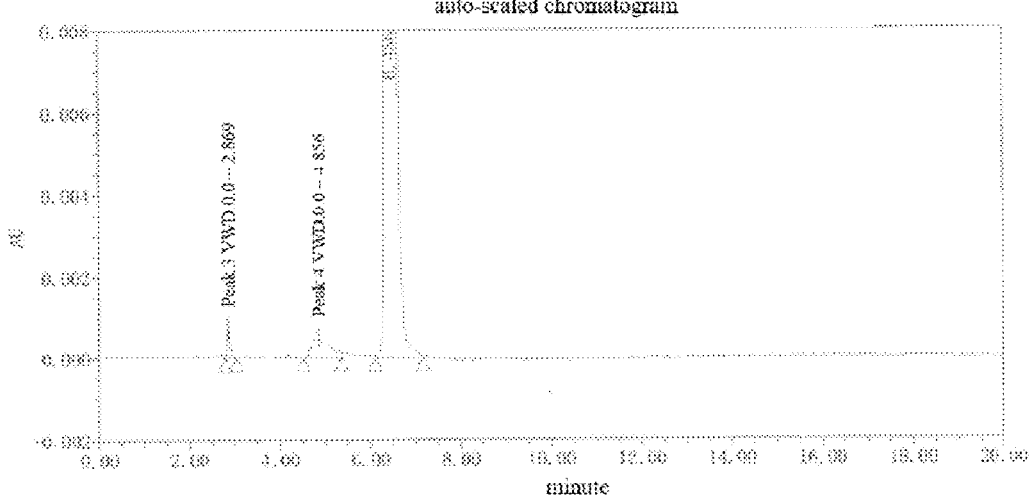

Peak Result

| | Name | Retention Time (Min) | Area (µV*S) | Height (µV) | %Area | Resolution | USP Number of Theoretical Plates |
|---|---|---|---|---|---|---|---|
| 1 | Peak    1 VWD.0.0 | 2.605 | | | | | |
| 2 | Peak    2 VWD.0.0 | 2.640 | | | | | |
| 3 | Peak    3 VWD.0.0 | 2.869 | 3678 | 760 | 0.30 | | 9368 |
| 4 | Peak    4 VWD.0.0 | 4.856 | 13600 | 480 | 1.09 | 4.4 | 414 |
| 5 | Peak    5 VWD.0.0 | 5.340 | | | | | |
| 6 | | 6.456 | 1226635 | 129210 | 98.61 | 3.1 | 10943 |

Figure 7

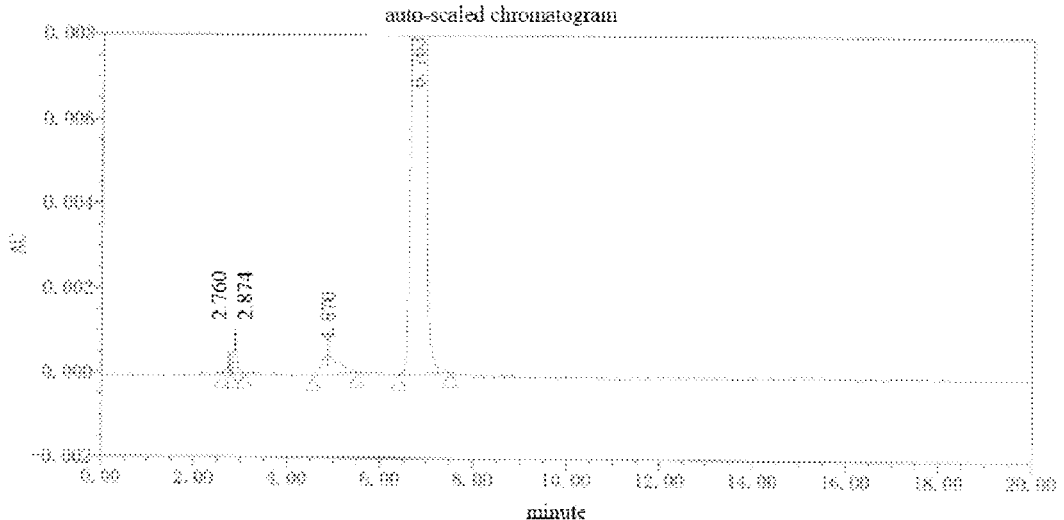

| | Sample Information | | |
|---|---|---|---|
| Sample Name | 181234-5     relevant substance | Sample Collector | zhangjianye |
| Sample Type | Unknown | Sample Group Name | active    pharmaceutical    ingredient test20181222 |
| Vial Number | 1:D,2 | Collecting Method Group | BHSZXALDP_HL_YGWZ_QC055a |
| Number   of   Sample Feeding | 1 | Processing Method | levamlodipine besylate hydrate relevant substance |
| Volume of Sample | 20.00 ul | Channel Name | VWD.0.0 |
| Operation Time | 20.0 Minutes | Processing         Channel Annotation | VWD: Signal A, 238 nm |
| Collection Time | 23 December 2018, 9:58:38 CST | | |
| Processing Time | 23 December 2018, 14:47:55 CST | | | auto-scaled chromatogram minute

Peak Result

| | Name | Retention Time (Min) | Area (µV*S) | Height (µV) | %Area | Resolution | USP Number of Theoretical Plates |
|---|---|---|---|---|---|---|---|
| 1 | | 2.760 | 1058 | 259 | 0.08 | | 14195 |
| 2 | | 2.874 | 3794 | 788 | 0.29 | 1.1 | 9482 |
| 3 | | 4.870 | 12239 | 451 | 0.94 | 4.7 | 421 |
| 4 | | 6.763 | 1287528 | 130357 | 98.69 | 3.8 | 11041 |

Figure 8

COMPOSITION CONTAINING LEVAMLODIPINE BESYLATE HYDRATE AND ITS PREPARATION METHOD

CROSS-REFERENCE TO RELATED APPLICATION:

This application is the National Stage of International Application No. PCT/CN2020/123670, filed Oct. 26, 2020, and claims benefit of Chinese Patent Application No. 201911137739.6, filed Nov. 8, 2019, the full contents of all of which are hereby incorporated by reference in their entirety.

TECHNICAL FIELD

The present invention relates to the technical field of levamlodipine besylate, in particular to a composition containing levamlodipine besylate hydrate, its preparation method, pharmaceutical preparations and use.

BACKGROUND ART

Amlodipine was developed by Pfizer in the United States and entered the Chinese market under the brand name "Norvasc" in 1994 as a drug for treating hypertension and angina pectoris. Amlodipine is a racemate consisting of levamlodipine and dextroamlodipine, and the pharmacological functions thereof are different. Dexamlodipine lacks calcium channel blocking activity and is a potent inhibitor of smooth muscle cell migration; levamlodipine is a long-acting calcium channel antagonist, and has the effect of treating hypertension and angina pectoris. Therefore, in the prior art, there have been technologies in which amlodipine is separated to obtain levamlodipine for treating hypertension and angina pectoris based on its long-acting calcium ion antagonism (for example, WO9525722A1, WO0160799A1, WO9310779A1).

Amlodipine in its free base form exhibits low stability and is therefore preferably administered in the form of a pharmaceutically acceptable acid addition salt. Therefore, different acid addition salts of levamlodipine have been developed, such as levamlodipine besylate, levamlodipine maleate, levamlodipine nicotinate, levamlodipine aspartate and the like.

In preparing the corresponding hydrates of amlodipine or levamlodipine salts, it is often necessary to use organic solvents. For example, WO03089414A1 discloses amlodipine nicotinate dihydrate, which was prepared by recrystallization of amlodipine and nicotinic acid in a mixed solvent of methanol and isopropanol or water and isopropanol. CN101495451A discloses the preparation of levamlodipine camphorsulfonate hydrate, which was by adding levamlodipine free base to a mixture of isopropanol and distilled water, adding camphorsulfonic acid thereto, stirring, filtering and washing with isopropanol and distilled water. CN102342937A discloses the preparation of amlodipine maleate hydrate, and the solvents used therein were ethanol, dimethyl sulfoxide and deionized water. WO2007017538A2 discloses a method for treating amlodipine besylate with isopropanol to obtain its crystals. JP2007015978A discloses that amlodipine besylate was obtained by reacting amlodipine base with benzenesulfonic acid monohydrate in ethyl acetate. KR20120066691A discloses adding an ethanol solution of benzenesulfonic acid to an ethanol solution of levamlodipine, adding water after stirring for 2 hours, filtering and washing with water to obtain levamlodipine benzenesulfonate hydrate. In the methods for preparing levamlodipine besylate hydrate disclosed in CN105111137B and CN102659672B, both of the crystallization processes involved the use of organic solvents.

It can be seen that most of the prior art technologies use organic solvents to prepare levamlodipine besylate hydrate. There are also some technologies for preparing levamlodipine besylate hydrate or amlodipine besylate hydrate using an aqueous media.

WO03/043635A1 discloses the use of water to prepare the hydrate of amlodipine besylate salt in water. But amlodipine besylate or amlodipine and benzenesulfonic acid hydrate were used, not levamlodipine and benzenesulfonic acid. CN1152013C discloses placing levamlodipine in water, adding benzenesulfonic acid and stirring, heating under nitrogen protection, then cooling, crystallizing overnight, and then filtering and washing to obtain levamlodipine besylate hydrate. The performance parameters of this product in a pharmaceutical preparation were not studied and no specific levamlodipine besylate hydrate composition with suitable properties was provided. WO2006/043148A1 discloses a method for separating the levorotatory and dextrorotatory forms from amlodipine racemates, and describes the use of a mixture of dimethylformamide solvate of levamlodipine-L-hemitartrate and water, to which an aqueous solution of benzenesulfonic acid was added, stirred under nitrogen while temperature was raised, cooled to room temperature and crystallized overnight to obtain levamlodipine besylate dihydrate. The method requires the preparation of the dimethylformamide solvate of levamlodipine-L-hemitartrate first. These technical solutions only describe the levoamlodipine salt or its hydrate form in passing in the process of isolating the levo isomer, relate to amlodipine sulfonate rather than levamlodipine sulfonate, or only describe the method for preparing the hydrates.

However, none of these technical solutions has optimized the method for preparing levamlodipine besylate hydrate in pure water. Also, none of them has studied the dissolution and stability of the prepared compositions containing levamlodipine besylate hydrate as well as various properties of the pharmaceutical preparations obtained by formulating the hydrate compositions. It can be seen that the prior art lacks studies on the preparation method of a levamlodipine besylate hydrate composition in pure water and the relevant performance and effect of the hydrate composition in drug formulation. Furthermore, none of them provides a composition product of levamlodipine besylate hydrate with more beneficial effects in drug formulation based on these research results.

In addition, it is known in the prior art that amlodipine besylate has poor solubility and a low dissolution rate in pharmaceutical preparations, which is not conducive to rapid onset of action. It often requires special preparation processing steps, such as micronization, the preparation process of spray granulation of amlodipine besylate and lactose solution on a two-fluid nozzle spray dryer (for example, CN103006600A), or adding a disintegrant, but such preparation processes often reduce the stability of the pharmaceutical preparations due to the processes such as disintegrant and micronization etc.

Contents of the Invention

SUMMARY OF THE INVENTION

It is found in the present invention that the crystalline water content of a levamlodipine besylate hydrate composition and its dissolution in a pharmaceutical preparation are related. The present invention has screened and determined the range of the crystalline water content of a levamlodipine besylate hydrate composition suitable for industrial application, and the range of the crystalline water content of a levamlodipine besylate hydrate composition with greater stability. The present invention also provides a safe, simple, environment-friendly, and low-cost preparation method for the above-said levamlodipine besylate hydrate compositions with those desired technical effects.

An object of the present invention is to provide a composition of levamlodipine besylate hydrate. Said composition is prepared in pure water. Pharmaceutical preparations prepared by using the composition have a high dissolution amount and good stability.

Specifically, the composition of levamlodipine besylate hydrate prepared according to the present invention has the following beneficial effects: the hydrate composition prepared according to the present invention has no residual organic solvent components; the composition of levamlodipine besylate hydrate has better thermal stability; the solid-form preparations made from the hydrate composition have a better dissolutionamount; and it is suitable for large-scale industrial production.

Another object of the present invention is to provide a preparation method of said composition of levamlodipine besylate hydrate.

Further, the present invention provides a preparation method of an optimized composition of levamlodipine besylate hydrate.

Another object of the present invention is to provide a pharmaceutical preparation of a composition of levamlodipine besylate hydrate.

Further, the present invention provides a combination preparation comprising a levamlodipine besylate hydrate composition. A preferred combination preparation comprises a levamlodipine besylate hydrate composition and folic acid. Another preferred combination preparation comprises a levamlodipine besylate hydrate composition and bisoprolol fumarate, or comprises a levamlodipine besylate hydrate composition, bisoprolol fumarate and folic acid.

Another object of the present invention is to provide an oral liquid preparation of a composition of levamlodipine besylate hydrate.

Another object of the present invention is to provide the pharmaceutical use of the above-mentioned levamlodipine besylate hydrate composition, and the single-active-ingredient and combination preparations comprising the composition. Said use refers to the use as a long-acting calcium ion antagonist for treating hypertension, angina pectoris, and related diseases.

DETAILED DESCRIPTION OF THE INVENTION

The composition of levamlodipine besylate hydrate of the present invention is a composition of levamlodipine besylate hydrate with different crystalline water content.

The preparation of the composition is based on precipitating levamlodipine besylate hydrate in pure water without any organic solvent, and then drying under normal temperature and normal pressure.

The composition of levamlodipine besylate hydrate of the present invention has the chemical name of a composition of (4 s)-2-[(2-aminoethoxy)methyl]-4-(2-chlorophenyl)-6-methyl-1,4-dihydro-3,5-pyridinedicarboxylic acid-3-ethyl ester, 5-methyl ester benzenesulfonate hydrate.

Each compound in said composition of the levamlodipine besylate hydrate can be represented by the following structural formula:

The molecular formula of the compound contained in said composition is:

$$C_{20}H_{25}ClN_2O_5 \cdot C_6H_6O_3S \cdot nH_2O, 1 < n < 2.$$

The composition is prepared in pure water. It is found in the present invention that particles of a levamlodipine besylate hydrate composition containing relatively high crystalline water content become soft, and the active pharmaceutical ingredient(s) and the auxiliary materials easily stick together, which cannot meet the requirements of making pharmaceutical preparations. A hydrate composition with a crystalline water content of less than 5.8% can meet the requirements of making pharmaceutical preparations. Preferably, the crystalline water content of the hydrate composition is less than 5.5%.

It is also found in the present invention that the thermal stability of a levamlodipine besylate hydrate composition with a crystalline water content of more than 4.5% is better than products with a different crystalline water content.

It is also found in the present invention that the dissolution amount of the levamlodipine besylate hydrate composition is positively correlated with the crystalline water content of the composition. Thus, making pharmaceutical compositions of a levamlodipine besylate hydrate composition can lead to a better dissolution amount of a solid-form preparation.

Based on the above findings, the composition of levamlodipine besylate hydrate prepared according to the present invention has the following beneficial effects: the hydrate composition prepared according to the present invention does not contain levamlodipine besylate hydrate with ethanol or acetone, and does not produce benzenesulfonate ester genotoxic substances; the composition of levamlodipine besylate hydrate has better thermal stability; the solid-form preparations made from the hydrate composition have a better dissolution amount; suitable for industrial production and application.

The composition of levamlodipine besylate hydrate with the above beneficial effects, wherein the hydrate compounds contained have different numbers of crystalline water molecules, the number of crystalline water molecules of each compound ranges from 1 to 2, and the crystalline water content is in the range of 3-6%. A preferred crystalline water content is 3-5.8%, a more preferred crystalline water content is 4.0-5.5%, an even more preferred crystalline water content is 4.4-5.5%, a yet more preferred crystalline water content is 4.5-5.4%.

The preparation method of the composition of levamlodipine besylate hydrate of the present invention is to stir and heat benzenesulfonic acid and levamlodipine in an aqueous solution to form a salt and dissolve, and the product is precipitated by cooling and crystallization. Excess benzenesulfonic acid remains in the solution to obtain pure levamlodipine benzenesulfonate hydrate, which is centrifugally washed with an appropriate amount of water, and dried at normal temperature to obtain a product with different crystalline water content. The powder is not a pure compound but a composition. It is the composition of levamlodipine besylate hydrate that is prepared by this method.

By selecting a mixed solvent of ethanol and water, levamlodipine besylate ethanol hydrate containing 2.5 crystalline water molecules can be prepared. Levamlodipine besylate ketone/alcohol hydrate containing 1.5 crystalline water molecules can be prepared in mixed solvents of acetone and water, isopropanol and water and propylene glycol and water, respectively. However, the above methods all contain a certain amount of organic solvents. Benzenesulfonic acid and alcohols can form sulfonate ester compounds, which are genotoxic. Acetone itself is toxic.

What crystallizes in pure water at –5° C. ~ 10° C. is levamlodipine besylate hydrate. The crystals are flaky crystals and are brittle. Place the crystallization solution on a glass dish, and it can be seen that the crystals are in a state similar to porridge. During the centrifugation process, the crystals stick together, and the encapsulated water can account for 25% of the mass after drying. This part of the water cannot be removed by centrifugation, which indicates that the crystals have low mechanical strength, are soft and have stickiness. Compounds that still contain crystalline water after drying are gradually heated and the sample softens until it becomes a viscous mass rather than a liquid.

The production method of the optimized composition of levamlodipine besylate hydrate of the present invention is: weighing benzenesulfonic acid and levamlodipine, benzenesulfonic acid; levamlodipine molar ratio=1-1.05, weighing purified water and adding to a neutralization vessel through a feeding port, raising temperature to 46° C., and adding pharmaceutical raw materials benzenesulfonic acid and levamlodipine until levamlodipine solid dissolves and disappears. The aqueous solution is placed in a tank for crystallization, and temperature is controlled to be within a range of –5° C. to 10° C., the preferred temperature is –5° C. to 1° C. and time is ≥12 hours, followed by centrifugal filtration, and centrifugally washed with a small amount of nearly purified water. Then it is dried at room temperature, and to produce a composition of levamlodipine besylate hydrate with a crystalline water content which is controlled to be within a range of 3-6%, preferably about 5%, more preferably 4-5.8%, even more preferably 4.5-5.5%, yet more preferably 4.5%-5.4%. The levamlodipine besylate with the crystalline water content of 3-6%, 4-5.8%, 4.5-5.5%, and 4.5-5.4% has 1-2 crystalline water molecules.

Even with the efforts of professionals, it is currently still impossible to grow single crystals of levamlodipine besylate hydrate in pure water.

The present invention also relates to a levamlodipine besylate hydrate composition prepared by the above method.

The present invention also relates to a pharmaceutical preparation of a composition of levamlodipine besylate hydrate. Said pharmaceutical preparation of a composition of levamlodipine besylate hydrate can be any pharmaceutically acceptable preparation such as a tablet, a capsule, a sustained-release preparation, an oral liquid, a fast-sustained-release preparation, a controlled-release preparation, a microcapsule, microsphere, a liposome, etc., prepared by using said hydrate composition and auxiliary materials known in the art as raw materials.

The composition of levamlodipine besylate hydrate of the present invention can be used to prepare various single-active-ingredient and combination preparations suitable for oral consumption.

The present invention also relates to a combination preparation comprising a levamlodipine besylate hydrate composition and folic acid. In the combination preparation, the mass ratio of the levamlodipine besylate hydrate composition to folic acid is: 2-3 (levamlodipine besylate hydrate calculated in levamlodipine, the same below): 0.1-1.2, preferably 2.5:0.4.

The combination preparation with the composition of levamlodipine besylate hydrate and folic acid as active ingredients can significantly reduce blood pressure and homocysteine at the same time when used to treat patients with grade I and II H-type hypertension, and significantly improve the carotid intima-media thickness, slow down the rate of atherosclerosis progression, and effectively reduce the occurrence of cerebrovascular events. The combination preparation can not only treat hypertension, but also reduce the occurrences of cerebrovascular events, so that patients with hypertension can improve their quality of life and prolong their lifespan.

The present invention also relates to a combination preparation comprising a levamlodipine besylate hydrate composition, bisoprolol fumarate, and/or folic acid. In the combination preparation, the mass ratio of the levamlodipine besylate hydrate composition to bisoprolol fumarate to folic acid is: 2-3 (levamlodipine besylate hydrate calculated in levamlodipine, the same below): 2-3:0.1-1.2, preferably 2.5:2.5:0.4.

The present invention also provides an oral liquid preparation of a composition of levamlodipine besylate hydrate. The levamlodipine besylate hydrate composition prepared by pure water in the present invention does not contain any organic solvent residues for preparation of an oral liquid, and does not need any adjuvant to be added.

The levamlodipine besylate hydrate composition is dissolved in pure water, the mass ratio of levamlodipine besylate to pure water is 1-10 (levamlodipine besylate hydrate calculated in levamlodipine, the same below): 1-15, preferably 1-5:1.2-7, more preferably 2-3:3-4, more preferably 2.5:3.5. For example: using a levamlodipine besylate hydrate composition calculated as 2.5 mg of levamlodipine, dissolved in 3.5 mg of pure water. Due to the bitter taste of levamlodipine besylate, flavoring agent(s) can be appropriately added, for example aspartatyl chloride phenylalanine methyl ester, which is a dipeptide sweetener with high safety, does not require insulin to metabolize, does not cause dental caries, and effectively reduces calorie intake, included in the US Pharmacopeia XXIII edition, the dosage weight concentration range being 0.1% to 0.6%, suitable for patients with diabetes and obesity. For children's medication, an appropriate amount of liquid may be withdrawn with a straw for oral consumption.

Specifically, the present invention relates to a fast-sustained-release preparation of levamlodipine besylate, the formulation of which is as follows in mass ratios: the sustained-release layer comprising: levamlodipine besylate calculated in levamlodipine 4-5, polyvinylpyrrolidone 30-40, hydroxypropyl cellulose 55-65, microcrystalline cellulose 17-30, and magnesium stearate 0.1-1; the fast-release layer comprising:plevamlodipine besylate calculated in levamlodipine 1-2, microcrystalline cellulose 40-45, pregelatinized starch 35-45, cross-linked polyvinylpyrrolidone 1-8, polyvinylpyrrolidone 5-15, and magnesium stearate 0.1-1.

Preferably, the formulation of said levamlodipine besylate fast-sustained-release preparation is as follows in mass ratios: the sustained-release layer comprising:plevamlodipine besylate calculated in levamlodipine 4.5, polyvinylpyrrolidone 35, hydroxypropyl cellulose 60, microcrystalline cellulose 23.9, magnesium stearate 0.5; the fast-release layer comprising: levamlodipine besylate calculated in levamlodipine 1.5, microcrystalline cellulose 40.5, pregelatinized starch 40, cross-linked polyvinylpyrrolidone 5, polyvinylpyrrolidone 10, and magnesium stearate 0.5.

The present invention also relates to a fast-sustained-release preparation of a combination preparation of levamlodipine besylate and folic acid, the formulation of which is as follows in mass ratios: the sustained-release combination layer comprising:plevamlodipine besylate calculated in levamlodipine 4-5, polyvinylpyrrolidone 30-40, hydroxypropyl cellulose 55-65, microcrystalline cellulose 17-30, and magnesium stearate 0.1-1; the fast-release combination layer comprising: levamlodipine besylate calculated in levamlodipine 1-2, folic acid 0.1-1, microcrystalline cellulose 40-45, pregelatinized starch 35-45, cross-linked polyvinylpyrrolidone 1-8, polyvinylpyrrolidone 5-15, and magnesium stearate 0.1-1.

Preferably, the formulation of the levamlodipine besylate fast-sustained-release preparation in mass ratios is: the sustained-release combination layer comprising:levamlodipine besylate calculated in levamlodipine 4.5, polyvinylpyrrolidone 35, hydroxypropyl cellulose 60, microcrystalline cellulose 23.9, and magnesium stearate 0.5; the fast-release combination layer comprising: levamlodipine besylate calculated in levamlodipine 1.5, folic acid 0.4, microcrystalline cellulose 40.5, pregelatinized starch 40, cross-linked polyvinylpyrrolidone 5, polyvinylpyrrolidone 10, and magnesium stearate 0.5.

The present invention also relates to the pharmaceutical use of the above-mentioned levamlodipine besylate hydrate composition, and the single-active-ingredient and combination preparations comprising the composition. Said pharmaceutical use refers to its use as a long-acting calcium antagonist for the treatment of hypertension, angina pectoris and other related diseases.

BRIEF DESCRIPTION OF THE DRAWINGS

FIG. 3: a chromatogram of sample 1 (crystalline water content 2.0%) placed in a 45° C. oven for 0 days FIG. 4: a chromatogram of sample 1 (crystalline water content 2.0%) placed in a 45° C. oven for 5 days FIG. 5: a chromatogram of sample 2 (crystalline water content 4.5%) placed in a 45° C. oven for 0 days FIG. 6: a chromatogram of sample 2 (crystalline water content 4.5%) placed in a 45° C. oven for 5 days FIG. 7: a chromatogram of sample 3 (crystalline water content 5.4%) placed in a 45° C. oven for 0 days FIG. 8: a chromatogram of sample 3 (5.4% water of crystallization) placed in a 45° C. oven for 5 days

SPECIFIC MODES FOR CARRYING OUT THE INVENTION

Figure 1:
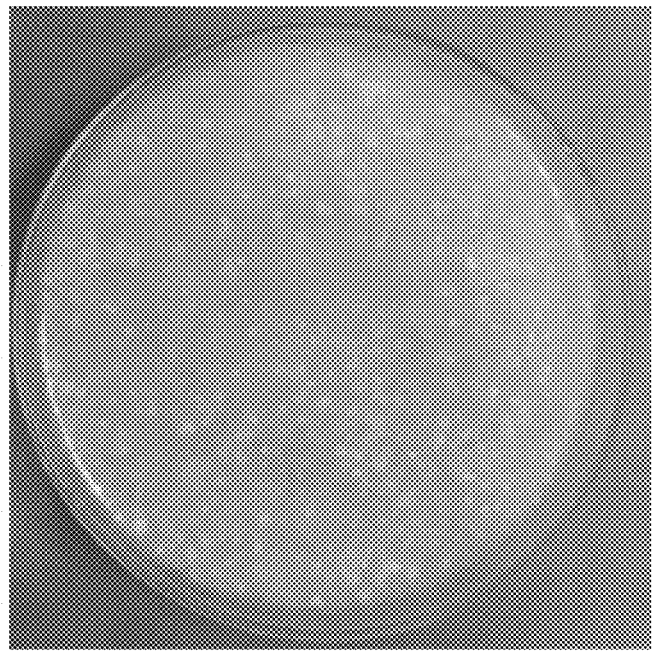
FIG. 1: a photo of the porridge-like crystals of levamlodipine besylate hydrate in water

Example 1 Preparation and Physical and Chemical Parameter Test of Levamlodipine Besylate Hydrate Composition Satisfying Requirements of Solid-Form Preparation Plain Tablets Preparation of Levamlodipine Besylate Hydrate Composition Weigh 51 kilograms of purified water, put the purified water into a reactor through a feeding port and stir, heat up to 46° C., add 1.60 kilograms of levamlodipine, and an aqueous solution with 0.65 kilograms of benzenesulfonic acid dissolved in 0.2 kilograms of water. The molar ratio of levamlodipine to benzenesulfonic acid is about 1:1.05 to ensure that all levamlodipine reacts with benzenesulfonic acid to generate organic salts. The total amount of purified water is 51.2 kilograms, which is 32 times the feeding amount of levamlodipine. After completely dissolving, it is transferred to a crystallization bucket, placed in a freezer for crystallization, and the crystals are porridge-like in water, see FIG. 1, temperature controlled to be within the range of-5° C. to 10° C., the temperature in this experiment is controlled at −5° C., the time is ≥12 hours, and then centrifuged at a speed of 2000 r/min, and filtered. Then rinse with 2 kg of purified water: after stopping the centrifuge, pour the purified water on the surface of the filter bag, then start the centrifuge machine to centrifuge, and then dry. Room temperature: 20° C., humidity: 52%, air flow through the through-air oven: 12000 m³/hour, drying temperature 30±2° C., drying time 1.5 hours, crystalline water content 5.3%.

Test of Physical and Chemical Parameters of the Levamlodipine Besylate Hydrate Composition Single crystals of levamlodipine besylate acetone hydrate and levamlodipine besylate ethanolate hydrate containing 1.5 crystalline wate molecules and 2.5 crystalline water molecules and containing organic solvents can be prepared in acetone+water and ethanol+water, respectively. However, the single crystals of levamlodipine besylate hydrate cannot be crystallized in pure water yet, and only a composition of levamlodipine besylate hydrate can be produced. The data of the powder of the composition prepared by the method of the present invention is similar to the simulated powder data of the single crystals of the above-mentioned levamlodipine besylate with 1.5 crystalline water molecules and 2.5 crystalline water molecules. The test conditions are as follows:

The X-ray powder diffractometer model D8 Advance used is an apparatus from Bruker, Germany. The samples are, respectively: the composition of levamlodipine besylate hydrate prepared in Example 1, single crystals of levamlodipine besylate with 1.5 crystalline water molecules, and single crystals of levamlodipine besylate with 2.5 crystalline water molecules.

Figure 2:
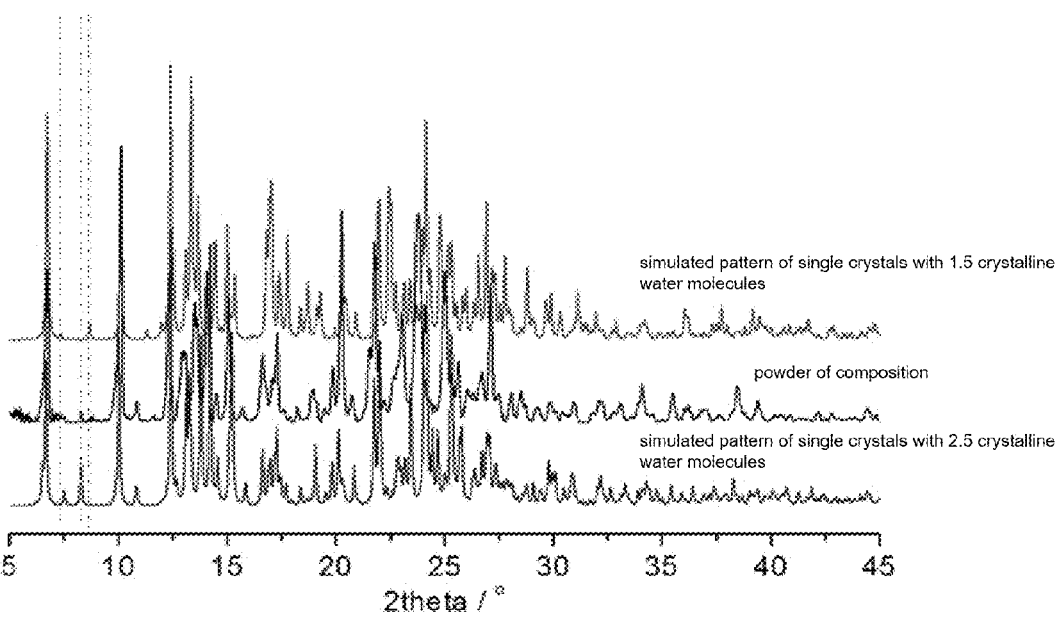
FIG. 2: powder diffraction patterns of levamlodipine besylate hydrate compositions, in the figure from top to bottom are the reference standard's simulated powder diffraction pattern of levamlodipine besylate with 1.5 crystalline water molecules (crystallization solvent actone+water), the powder diffraction pattern of a levamlodipine besylate hydrate composition produced according to the present invention, the reference standard's simulated powder diffraction pattern of levamlodipine besylate with 2.5 crystalline water molecules (crystallization solvent ethanol+water)

Test method of the crystal form of levamlodipine besylate powder: place the powder sample on the sample plate and flatten it, and use the D8 Advance instrument to collect the diffraction data. Instrument setup parameters: Cu target source (Kα), wavelength λ=1.5406 Å. The test voltage and current are 40 kV and 40 mA respectively, the test range is 5-45°, and the scanning speed is 0.02°/s. The powder diffraction data collected are directly compared to powder data simulated from the X-ray single crystal data of the reference standards containing 2.5 and 1.5 water molecules. The simulated powder data of the reference standards are based on X-single crystal data, and are obtained using Mercury software. The diffraction results are shown in FIG. 2. It can be seen that the crystalline water content of the levamlodipine besylate hydrate composition powder is between levamlodipine besylate with 1.5 crystalline water molecules and levamlodipine besylate with 2.5 crystalline water molecules.

Example 2 Production of Levamlodipine Besylate Hydrate Composition with Specific Crystalline Water Content The unseparated levamlodipine besylate hydrate prepared in pure water should be a compound with a fixed proportion of crystalline water, which is difficult to industrially produce on a large scale. Because one of the crystalline water molecules has a low dissociation temperature, that crystal water molecule is very easy to dissociate into the air. To keep the crystalline water content of the hydrate unchanged, the compound needs to be strictly kept at a relatively low temperature, under corresponding humidity and atmospheric pressure. Obviously, such prepared levamlodipine besylate hydrate is not pharmaceutically needed and is not suitable for the requirements of direct compression. However, the preparation of a levamlodipine besylate hydrate composition can meet the requirement % of various types of pharmaceutical preparation %.

The stability of the levamlodipine besylate hydrate composition is related to temperature. Obviously, the lower the temperature, the more stable the compound. Levamlodipine besylate hydrate compositions with corresponding crystalline water content can be obtained under the drying conditions of Example 1, and meet the requirements of relevant quality standards.

TABLE 1

| Drying Time and Water Content | |
| --- | --- |
| Drying Time (mins) | H$_2$O% |
| 0 | 20.9 |
| 5 | 18.9 |
| 10 | 16.1 |
| 15 | 14.2 |
| 20 | 12.1 |
| 25 | 9.3 |
| 30 | 8.5 |
| 35 | 8.2 |
| 40 | 7.9 |
| 45 | 7 5 |
| 50 | 7.1 |
| 55 | 6.9 |
| 60 | 6.7 |
| 65 | 6.6 |
| 70 | 6.4 |
| 75 | 6.2 |
| 80 | 5.8 |
| 85 | 5.6 |
| 90 | 5.3 |
| 95 | 5.1 |
| 100 | 4.8 |

TABLE 1-continued

| Drying Time and Water Content | |
| --- | --- |
| Drying Time (mins) | H$_2$O% |
| 105 | 4.6 |
| 110 | 4.4 |
| 115 | 4.2 |

To obtain a levamlodipine besylate composition with lower crystalline water content requires lower air humidity to reduce drying time. The lower the crystalline water content of the levamlodipine besylate composition, the more voids the dissociated crystalline water will leave on the particle surface of the levamlodipine besylate composition, the larger the contact area between levamlodipine besylate and oxygen in the air, the more opportunities for oxidation reaction to occur, which is not conductive to long-term storage of pharmaceutical preparations.

Example 3 Material Properties of Levamlodipine Besylate Hydrate Composition Granules In order to meet the requirements for the production of solid-form preparation plain tablets, the preparation is a direct compression method. As such, the granules of the active pharmaceutical ingredient need to pass through a sieve below 10 mesh to ensure content uniformity. The granules of the levamlodipine besylate hydrate composition needs to be finished, and the particle size for the finishing of granulation is controlled to be 10 mesh. The levamlodipine besylate hydrate composition with a relatively high crystalline water content is soft, and they easily stick together during the finishing of granulation process and cannot meet the requirements of the finishing of granulation. A hydrate composition with a crystalline water content of less than 5.8% can meet the requirements of the finishing of granulation.

The composition of levamlodipine besylate hydrate with a crystalline water content of 3-6% prepared in Example 1 is dried to obtain compositions of levamlodipine besylate hydrate with different crystalline water content. By testing its physical properties, it is found that the granules of the samples with a crystalline water content of more than 5.8% become soft, and the active pharmaceutical ingredient and auxiliary materials easily stick together, which is not suitable for making pharmaceutical preparations. The crystalline water content of the hydrate being controlled below 5.5% can better meet the requirements of making pharmaceutical preparations.

1. Production of Samples: the method of Example 2 is used to prepare samples with corresponding water content.

2. Results:

TABLE 2

| Granulation Results | | | |
| --- | --- | --- | --- |
| Sample | | | |
| Crystalline Water Content % | Number of Crystalline Water Molecules | Stickiness | Sieving Performance |
| 6.0% | 2.01 | stickiness between particles | The materials which pass through the sieve stick together even when slightly squeezed |

TABLE 2-continued

| | | | |
|---|---|---|---|
| Granulation Results | | | |

| Sample | | | |
|---|---|---|---|
| Crystalline Water Content % | Number of Crystalline Water Molecules | Stickiness | Sieving Performance |
| 5.9% | 1.98 | stickiness between particles | The materials which pass through the sieve are less sticky when slightly squeezed |
| 5.8% | 1.94 | essentially no stickiness between particles | The materials which pass through the sieve have essentially no stickiness |
| 5.5% | 1.83 | no stickiness between particles | The materials which pass through the sieve have no stickiness |

Example 4 Thermal Stability of Levamlodipine Besylate Hydrate Compositions

Using the method of Example 2 of the present invention, compositions with different crystalline water content can be prepared and used as samples to test thermal stability.

The samples are placed in amber glass bottles, placed in an oven, and the temperature is adjusted to 45° C., and the relevant substances are tested after settled for 5 days.

The test method is as follows: The chromatographic conditions and system applicability test: Use octadecylsilane-bonded silica gel as the filler; methanol-0.03 mol/L potassium dihydrogen phosphate solution (75:25) as the mobile phase, the detection wavelength is 238 nm, the number of theoretical plates should be no less than 500 calculated in levamlodipine.

Preparation of the Test Solution: Take about 17 mg of this product, precisely weigh it, put it in a 100 ml volumetric flask, add a mobile phase to dissolve and dilute to the mark, shake well, precisely measure 5 ml, put it in a 25 ml volumetric flask, add a mobile phase to the mark, shake well to obtain the solution.

Determination Method: Precisely measure 10 μl of the reference solution and the test solution, inject into the liquid chromatography machine, record the chromatogram, measure the peak area, and calculate by the external standard method.

The test data is as follows:

TABLE 3

| | | impurities Before Heating of Sample | | Sample Placed in 45° C. Oven for 5 Days | |
|---|---|---|---|---|---|
| Sample Name | Crystalline Content Water | Retention Time of Impurities | Impurity Content | Retention Time of Impurities | Impurity Content |
| Sample 1 | 2.0% | — | None | 4.304 min | 0.07% |
| Sample 2 | 4.5% | — | None | — | None |
| Sample 3 | 5.4% | — | None | — | None |

Chromatograms of samples 1-3 after being placed in a 45° C. oven for 5 days are shown in FIGS. 3 to 8.

It can be seen that the levamlodipine besylate hydrate prepared in pure water is filtered and dried, and in the obtained product, the thermal stability of the levamlodipine besylate hydrate composition with a crystalline water content of 4.5-5.4% is better than other compositions with a different crystal water content. There is no obvious change in the appearance of sample 1. After the partial loss of the crystalline water, no fusion occurs between the particles, and the voids left inside the particles are prone to oxidation. For samples 2 and 3, less crystalline water is lost, less voids are left inside the particles, and the degree of oxidation is reduced.

The precipitated crystals obtained from the preparation of levamlodipine besylate in pure water is a hydrate, levamlodipine besylate hydrate of levamlodipine besylate and 2 crystalline water molecules. However, as shown in Example 3 above, for levamlodipine besylate hydrate with 2 crystalline water molecules, the active pharmaceutical ingredient and auxiliary materials easily stick together, which is not suitable for making pharmaceutical preparations. And for the levamlodipine besylate hydrate prepared by using an organic solvent and water, organic solvents such as alcohols, ketones, etc. will react with levamlodipine besylate to produce benzenesulfonate ester products in the preparation process. It is common knowledge in the art that benzenesulfonate esters are genotoxic (e.g., see Shao Xiaowei, Research on Genotoxicity Detection and Synthesis of Benzenesulfonate Esters, Jilin University Master Thesis, CNKI China Knowledge Network Master Thesis Database, published on May 1, 2019). In addition, in the prepared levamlodipine besylate hydrate product, organic solvent components will inevitably remain, and these organic components are harmful to various degrees. For example, it is common knowledge in the art that acetone has toxic effects to the nervous system and mucous membranes. To sum up, it can be seen that the hydrate prepared by using organic solvents contains organic molecules bonded thereto. Even though it can have improved stability by adjusting its crystalline water content, compared with the hydrate composition prepared by using pure water in the present invention, it does not have any pharmaceutical advantages due to its toxicity.

Example 5 Dissolution Amount of Solid-Form Preparation of Levamlodipine Besylate Hydrate Composition The levamlodipine besylate hydrate composition prepared by the method of Example 2 of the present invention, the hydrate composition has different crystalline water content, and is prepared as tablets according to the following formulation:

TABLE 4

| | |
|---|---|
| levamlodipine besylate hydrate composition (calculated in levamlodipine) | 2.5 mg/tablet |
| starch | 53.75 mg/tablet |
| dextrin | 41.25 mg/tablet |
| sodium starch glycolate | 25.00 mg/tablet |
| magnesium stearate | 1.20 mg/tablet |

Each tablet weighs about 125 mg. Weigh the active pharmaceutical ingredient and the auxiliary materials as required by the number of tablets according to the above formulation and mix them evenly→direct compression, wherein the starch passes through a 60 mesh sieve during granulation.

Test of Dissolution Amount of Levamlodipine Besylate Hydrate Composition Tablets (each tablet containing 2.5 mg of levamlodipine), Test Method for Dissolution Amount: Protect from light. Take this product, follow the test method for dissolution amount (Chinese Pharmacopoeia 2015 Edition Part Four General Principles 0931), use 200 ml of hydrochloric acid solution (9-1000) as the solvent, and operate at 50 revolutions per minute. After 30 minutes, take an appropriate amount of the solution, filter, take the filtrate in the middle of the filtration process as the test solution. In addition, take 17 mg of levamlodipine besylate hydrate reference substance, precisely weigh it, put it in a 100 ml volumetric flask, add 2 ml of methanol to dissolve, add hydrochloric acid solution (9→1000) to dilute to the mark, shake well, precisely measure 5 ml, put it in in a 50 ml volumetric flask, add hydrochloric acid solution (9→1000) to dilute to the mark, shake well, and use it as the reference solution.

Take the above two solutions, according to the spectrophotometry method (Chinese Pharmacopoeia 2015 Edition Part Four General Principles 0401), measure the respective absorbance at the wavelength of 238 nm, and calculate the dissolution amount of each tablet. The limit is 80% of the label amount, which should comply with the regulations.

The test results are as follows:

TABLE 5

| Item No. | Crystalline Water Content (%) | Dissolution Amount (%) | Item No. | Crystalline Water Content (%) | Dissolution Amount (%) | Item No. | Crystalline Water Content (%) | Dissolution Amount (%) | Item No. | Crystalline Water Content (%) | Dissolution Amount (%) |
|---|---|---|---|---|---|---|---|---|---|---|---|
| 1 | 1.3 | 89.0 | 40 | 3.9 | 95.9 | 79 | 4.1 | 92.6 | 118 | 4.3 | 92.1 |
| 2 | 1.6 | 93.3 | 41 | 3.9 | 94.3 | 80 | 4.1 | 98.1 | 119 | 4.3 | 92.7 |
| 3 | 1.7 | 91.1 | 42 | 3.9 | 90.8 | 81 | 4.1 | 94.4 | 120 | 4.3 | 93.1 |
| 4 | 1.7 | 92.9 | 43 | 3.9 | 90.0 | 82 | 4.1 | 91.6 | 121 | 4.4 | 88.8 |
| 5 | 1.7 | 87.8 | 44 | 3.9 | 95.7 | 83 | 4.1 | 89.8 | 122 | 4.4 | 95.3 |
| 6 | 1.7 | 94.2 | 45 | 3.9 | 95.3 | 84 | 4.1 | 88.7 | 123 | 4.4 | 91.1 |
| 7 | 1.7 | 94.3 | 46 | 3.9 | 92.8 | 85 | 4.1 | 93.3 | 124 | 4.4 | 97.3 |
| 8 | 1.8 | 95.0 | 47 | 3.9 | 91.2 | 86 | 4.1 | 94.2 | 125 | 4.4 | 97.7 |
| 9 | 1.8 | 90.8 | 48 | 3.9 | 96.7 | 87 | 4.2 | 90.3 | 126 | 4.4 | 97.4 |
| 10 | 1.8 | 87.6 | 49 | 3.9 | 96.7 | 88 | 4.2 | 92.9 | 127 | 4.4 | 91.5 |
| 11 | 1.9 | 91.2 | 50 | 3.9 | 95.8 | 89 | 4.2 | 92.5 | 128 | 4.4 | 91.6 |
| 12 | 1.9 | 87.0 | 51 | 3.9 | 96.1 | 90 | 4.2 | 97 6 | 129 | 4.4 | 91.8 |
| 13 | 2.0 | 87.5 | 52 | 3.9 | 93.8 | 91 | 4.2 | 97.9 | 130 | 4.4 | 91.7 |
| 14 | 2.4 | 99.2 | 53 | 3.9 | 96.5 | 92 | 4.2 | 97.1 | 131 | 4.4 | 94.4 |
| 15 | 2.7 | 92.0 | 54 | 3.9 | 90.0 | 93 | 4.2 | 93.1 | 132 | 4.4 | 97.9 |
| 16 | 3.0 | 93.0 | 55 | 4.0 | 93.4 | 94 | 4.2 | 94.1 | 133 | 4.5 | 96.3 |
| 17 | 3.2 | 96.4 | 56 | 4.0 | 92.0 | 95 | 4.2 | 96.1 | 134 | 4.5 | 92.5 |
| 18 | 3.2 | 96.4 | 57 | 4.0 | 94.4 | 96 | 4.2 | 89.1 | 135 | 4.5 | 92.3 |
| 19 | 3.3 | 93.7 | 58 | 4.0 | 93.3 | 97 | 4.2 | 95.5 | 136 | 4.5 | 89.6 |
| 20 | 3.5 | 90.8 | 59 | 4.0 | 94.5 | 98 | 4.2 | 95.5 | 137 | 4.5 | 96.3 |
| 21 | 3.4 | 87.7 | 60 | 4.0 | 95.7 | 99 | 4.2 | 95 9 | 138 | 4.5 | 89.4 |
| 22 | 3.4 | 93.1 | 61 | 4.0 | 94.7 | 100 | 4.2 | 92.4 | 139 | 4.5 | 90.1 |
| 23 | 3.5 | 90.2 | 62 | 4.0 | 97.7 | 101 | 4.2 | 95.2 | 140 | 4.5 | 92.5 |
| 24 | 3.5 | 95.2 | 63 | 4.0 | 96.2 | 102 | 4.2 | 97.0 | 141 | 4.6 | 92.9 |
| 25 | 3.5 | 92.3 | 64 | 4.0 | 90.7 | 103 | 4.2 | 97.9 | 142 | 4.6 | 93.0 |
| 26 | 3.5 | 95.6 | 65 | 4.0 | 98.1 | 104 | 4.3 | 91.1 | 143 | 4.6 | 95.4 |
| 27 | 3.5 | 96.0 | 66 | 4.0 | 93.6 | 105 | 4.3 | 92.2 | 144 | 4.6 | 95.3 |
| 28 | 3.5 | 94.0 | 67 | 4.0 | 88.7 | 106 | 4.3 | 96.1 | 145 | 4.6 | 93.2 |
| 29 | 3.5 | 93.7 | 68 | 4.0 | 88.1 | 107 | 4.3 | 90.4 | 146 | 4.6 | 96.3 |
| 30 | 3.5 | 89.1 | 69 | 4.0 | 93.9 | 108 | 4.3 | 97.3 | 147 | 4.6 | 94.3 |
| 31 | 3.5 | 95.8 | 70 | 4.1 | 93.5 | 109 | 4.3 | 95.6 | 148 | 4.6 | 94.0 |
| 32 | 3.5 | 96.4 | 71 | 4.1 | 96.5 | 110 | 4.3 | 94.8 | 149 | 4.6 | 96.3 |
| 33 | 3.5 | 95.6 | 72 | 4.1 | 97.0 | 111 | 4.3 | 91.4 | 150 | 4.6 | 92.9 |
| 34 | 3.6 | 95.1 | 73 | 4.1 | 96.9 | 112 | 4.3 | 92.8 | 151 | 4.6 | 95.8 |
| 35 | 3.6 | 92.5 | 74 | 4.1 | 88.9 | 113 | 4.3 | 93.6 | 152 | 4.8 | 92.4 |
| 36 | 3.7 | 92.9 | 75 | 4.1 | 94.9 | 114 | 4.3 | 94.4 | 153 | 4.8 | 89.8 |
| 37 | 3.7 | 94.8 | 76 | 4.1 | 95.0 | 115 | 4.3 | 91.0 | 154 | 4.9 | 89.4 |
| 38 | 3.8 | 89.9 | 77 | 4.1 | 96.9 | 116 | 4.3 | 92.4 | 155 | 5.0 | 90.7 |
| 39 | 3.8 | 91.3 | 78 | 4.1 | 93.5 | 117 | 4.3 | 95.7 | 156 | 5.2 | 93.7 |

TABLE 6

Linear Correlation Coefficients

Dependent Variable: Dissolution Amount (%) Independent Variable: Crystalline Water Content (%)

| | | | Model Summary | | | | |
|---|---|---|---|---|---|---|---|
| | | | Degree of | Degree of | | Coefficient Estimates | |
| Formula | $R^2$ | P | Freedom 1 | Freedom 2 | p-value | Constant | b1 |
| Linear | 0.038 | 6.144 | 1 | 154 | 0.014 | 90.776 | 0.696 |

Figure 9:
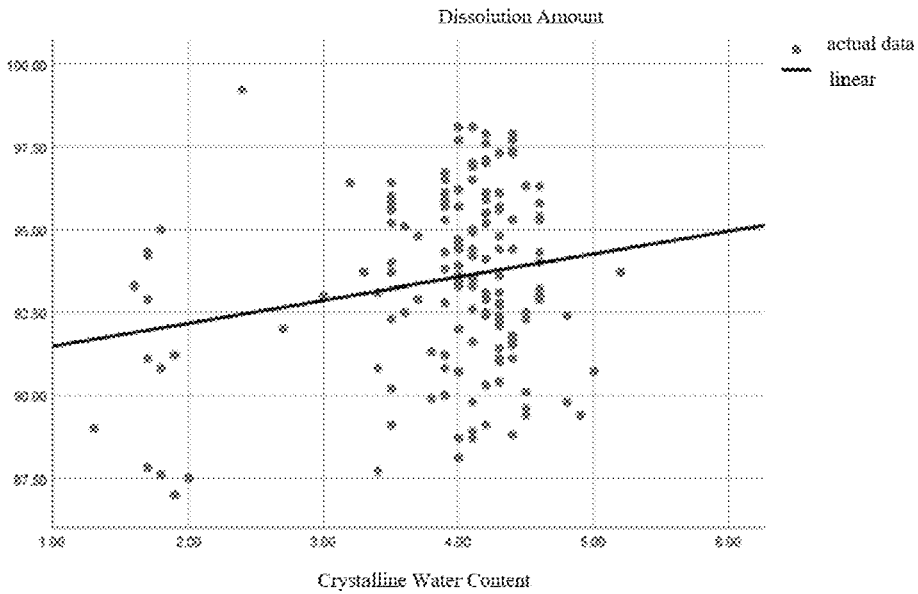
FIG. 9: the dissolution amount of tablets of the levamlodipine besylate hydrate compositions correlate with the crystalline water content of the hydrate.

The correlation diagram of the dissolution amount of the levamlodipine besylate hydrate composition tablets and the crystalline water content of the hydrate is shown in FIG. 9.

The above analysis shows that the dissolution amount is positively correlated to the crystalline water content of the composition. Obviously, the production of a pharmaceutical composition of the levamlodipine besylate hydrate composition can make a solid-form preparation have a better dissolution amount.

Example 6 Levoamlodipine Besylate Hydrate Composition or +Folic Acid Tablet Formulations

TABLE 7

Single-Active-Ingredient and Combination Tablet Formulations

| Single-Active-Ingredient Formulation | | Combination Tablet Formulation | |
|---|---|---|---|
| Materials of Sing-Active-Ingredient Formulation | mg/tablet | Materials of Combination Formulation | mg/tablet |
| calculated in levamlodipine | 2.5 2.5 | calculated in levamlodipine folic acid | 2.5 0.4 |
| anhydrous calcium hydrogen phosphate | 39.8 | anhydrous calcium hydrogen phosphate | 39.4 |
| microcrystalline cellulose | 79 | microcrystalline cellulose | 79 |
| sodium starch glycol ate | 2.5 | sodium starch glycolate | 2.5 |

TABLE 7-continued

Single-Active-Ingredient and Combination Tablet Formulations

| Single-Active-Ingredient Formulation | | Combination Tablet Formulation | |
|---|---|---|---|
| Materials of Sing-Active-Ingredient Formulation | mg/tablet | Materials of Combination Formulation | mg/tablet |
| magnesium stearate | 1.2 | magnesium stearate | 1.2 |

Each tablet weighs about 125 mg. The levamlodipine besylate used in this Example is the levamlodipine besylate hydrate composition prepared by the method of Example 1, but is not limited to the product of Example 1 in actual production and application. The levamlodipine besylate hydrate compositions protected by the present invention may all be used to make corresponding pharmaceutical preparations. According to the above formulation, weigh the active pharmaceutical ingredients and auxiliary materials as required by the number of the tablets and mix them even-ly→direct compression.

Combination tablets can also be compressed into double-layered tablets, that is, two active pharmaceutical ingredients are each mixed with auxiliary materials for double-layered tableting.

Example 7 Levoamlodipine Besylate Hydrate Composition+Bisoprolol Fumarate or +Folic Acid Tablet

TABLE 8

Combination and Triple-Active-Ingredient Tablet Formulations

| composition of levamlodipine besylate hydrate + bisoprolol fumarate | | composition of levamlodipine besylate hydrate + bisoprolol fumarate + folic acid tablet | |
|---|---|---|---|
| Materials of Combination Formulation | mg/tablet | Materials of Triple-Active-Ingredient Formulation | mg/tablet |
| calculated in levamlodipine | 2.5 | calculated in levamlodipine | 2.5 |
| calculated in bisoprolol | 2.5 | calculated in bisoprolol folic acid | 2.5 0.4 |
| anhydrous calcium hydrogen phosphate | 63 | anhydrous calcium hydrogen phosphate | 63 0. |
| microcrystalline cellulose | 124.65 | microcrystalline cellulose | 124.65 |
| sodium starch glycolate | 4 | sodium starch glycolate | 4 |
| magnesium stearate | 2 | magnesium stearate | 9 |

Each tablet weighs about 200 mg. The levamlodipine besylate used in this Example is the levamlodipine besylate hydrate composition prepared by the method of Example 1, but is not limited to the product of Example 1 in actual production and application. The levamlodipine besylate hydrate compositions protected by the present invention may all be used to prepare corresponding pharmaceutical preparations. According to the above formulation, weigh the active pharmaceutical ingredients and the auxiliary materials as required by the number of tablets and mix them evenly→direct compression.

Example 8 Levoamlodipine Besylate Hydrate
Composition+Folic Acid-Fast-Sustained-Release
Formulations

TABLE 9

| Single-Active-Ingredient or Combination Fast-Sustained-Release Formulations | | | |
|---|---|---|---|
| Levamlodipine Besylate Hydrate Composition Fast-Sustained-Release Formulation | | Levamlodipine Besylate Hydrate Composition + Folic Acid Fast-Sustained Release-Formulation | |
| Sustained-Release Layer (First Layer) | mg/tablet | Sustained-Release Combination Laver (First Layer) | mg/tablet |
| calculated in levamlodipine | 4.0 | calculated in levamlodipine | 4.5 |
| polyvinylpyrrolidone | 35 | polyvinylpyrrolidone | 35 |
| hydroxypropyl cellulose | 60 | hydroxypropyl cellulose | 60 |
| microcrystalline cellulose | 23.9 | microcrystalline cellulose | 23.9 |
| magnesium stearate | 0.5 | magnesium stearate | 0.5 |
| calculatedin levamlodipine | 1.5 | calculated in levamlodipine | 1.5 |
| | | folic acid | 0.4 |
| microcrystalline cellulose | 40.5 | microcrystalline cellulose | 40.5 |
| pregelatinized starch | 40 | pregelatinized starch | 40 |
| cross-linked polyvinylpyrrolidone | 5 | cross-linked polyvinylpyrrolidone | 5 |
| polyvinylpyrrolidone | 10 | polyvinylpyrrolidone | 10 |
| magnesium stearate | 0.5 | magnesium stearate | 0.5 |

Each bilayer tablet weighs about 220 mg. The levamlodipine besylate used in this Example is the levamlodipine besylate hydrate composition produced by the method of Example 1, but is not limited to the product of Example 1 in actual production and application. The levamlodipine besylate hydrate compositions protected by the present invention may all be used to prepare corresponding pharmaceutical preparations.

According to the above formulation, weigh the active pharmaceutical ingredients and auxiliary materials as required by the number of tablets and mix them evenly→direct compression. Each tablet contains levamlodipine besylate calculated in levamlodipine 6 mg+folic acid 0.4 mg.

late hydrate compositions protected by the present invention may all be used to prepare corresponding pharmaceutical preparations. Weigh the above materials→mix→encapsulate.

Example 10 Production of Oral Liquid Preparation of Levamlodipine Besylate Hydrate Composition Solid-form preparations are not suitable for children and people who have difficulty swallowing. An oral liquid of the levamlodipine besylate hydrate composition is suitable for all patients to take. Because levamlodipine besylate hydrate compositions are all suitable for production of oral liquid preparations, the oral liquids prepared by the levamlodipine

TABLE 10

| Example 9 Levoamlodipine Besylate Hydrate Composition + or Bisoprolol Fumarate or + Folic Add Capsule Formulations | | | | | |
|---|---|---|---|---|---|
| Single-Active-Ingredient Capsule Formulation | | Combination Capsule Formulation | | Triple-Active-Ingredient Capsule Formulation | |
| Materials of Single-Active-Ingredient Formulation | mg/tablet | Materials of Combination Formulation | mg/tablet | Materials of Triple-Active-Ingredient Formulation | mg/tablet |
| calculated in levamlodipine | 2.5 | calculated in levamlodipine | 2.5 | calculated in levamlodipine | 2.5 |
| | | calculated in bisoprolol | 2.5 | calculated in bisoprolol | 2.5 |
| anhydrous calcium hydrogen phosphate | 122.5 mg | anhydrous calcium hydrogen phosphate | 120 mg | anhydrous calcium hydrogen phosphate | 120 mg |

Each tablet weighs approximately 125 mg. The levamlodipine besylate used in this Example is the levamlodipine besylate hydrate composition prepared by the method of Example 1, but is not limited to the product of Example 1 in actual production and application. The levamlodipine besybesylate hydrate compositions do not contain organic solvent residues and do not need adjuvants to be added, 2.5 mg of a levamlodipine besylate hydrate composition is dissolved in 3.5 mg of pure water. Levamlodipine besylate is bitter in taste, and thus a flavoring agent may be added in an appropriate amount, such as aspartatyl chloride phenylalanine methyl ester, which is a dipeptide sweetener, with a sweetness of 180 ~X° C. 300 times that of sucrose, with good sweetness and high safety, its metabolism does not require insulin, does not cause dental caries, and effectively reduces calorie intake. It is included in USP XXIII edition, and the dosage concentration ranges from 0.1% to 0.6%, suitable for patients with diabetes and obesity.

For children's medication, an appropriate amount of liquid may be withdrawn with a straw for oral consumption.

Preparation process, take a levamlodipine besylate hydrate composition equivalent to 10 grams of levamlodipine+flavoring agent (for example, 14 grams of aspartyl chloride phenylalanine methyl ester) dissolved in purified water 14 L→stir→fill 4 ml amber glass bottle-cap the bottle. Storage temperature is cool. The levamlodipine besylate 10 animals in each group, fasted for 16 hours before use. Dosage: Oral administration: 1.2605, 1.0714, 0.910, 0.7141, 0.6580 (g/kg), intraperitoneal administration: 0.7743, 0.6582, 0.5594, 0.4755, 0.4042 (g/kg) dose gradient: 0.85. Route of administration: experimental methods of oral administration and intraperitoneal administration, 100 mice are selected, fasted for 16 hours, and randomly divided into 10 groups. Oral administration to the first 5 groups, and the dose being 0.35 ml/10 g; intraperitoneal administration to the latter 5 groups, and the dose being 0.2 ml/10 g. Observation of indicators: The animals are observed for 7 days after drug administration, and their toxic reactions and deaths are recorded. Animals display closed eyes, lethargy, sagging skin and sparse fur after 0 minutes of administration, and begin to die after 1 hour. Symptoms before death are balance disorders and convulsions etc., no significant changes are seen in postmortem examination.

TABLE 11

LD50 Results of Oral Administration (Bliss Method)

| Dose mg/kg | Logarithmic dose | Animal Number (number) | Daily Deaths (7 days) \|1\|2\|3\|4\|5\|6\|7\| | Number of Deaths (number) | Death Rate (%) | Experimental Probability Unit | Last Probability Unit | Regression Probability Unit | Deviation |
|---|---|---|---|---|---|---|---|---|---|
| 1260.5 | 3.1 | 10 | \|10\|0\|0\|0\|0\|0\|0\| | 10 | 100 | 6.96 | 7.18 | 7.18 | 0.000065 |
| 1071.4 | 2.03 | 10 | \|0\|8\|0\|0\|0\|0\|0\| | 8 | 80 | 5.84 | 6.14 | 6.14 | 0.000031 |
| 910 7 | 2.96 | 10 | \|0\|6\|0\|0\|0\|0\|0\| | 6 | 60 | 5.25 | 5.09 | 5.09 | −0.000004 |
| 774.1 | 2.89 | 10 | \|0\|2\|0\|0\|0\|0\|0\| | 2 | 20 | 4.16 | 4.05 | 4.05 | −0.000038 |
| 658.0 | 2.82 | 10 | \|0\|0\|0\|0\|0\|0\|0\| | 0 | 0 | 3.04 | 3.01 | 3.01 | −0.000072 | used in this Example is the levamlodipine besylate hydrate composition produced by the method of Example 1, but is not limited to the product of Example 1 in actual production and application. The levamlodipine besylate hydrate compositions protected by the present invention may all be used to produce corresponding pharmaceutical preparations.

Significance index G=0.2018 X50=2.9531 SX=0.0164 G is relatively small.

Heterogeneity check Ch2=1.07 Ch2.05=7.82 Sb=3.3878 No heterogeneity.

Converted into the composition of levamlodipine besylate hydrate (calculated in levamlodipine) is LD50=24.925±1.7542 mg/kg.

TABLE 12

LD of Intraperitoneal Administration, Results (Bliss Method)

| Dose mg/kg | Logarithmic dose | Animal Number (Number) | Daily Death(7 Days) \|1\|2\|3\|4\|5\|6\|7\| | Number of Deaths (Number) | Death Rate (%) | Experimental probability unit | Last probability Unity | Regression Probability Unit | deviation |
|---|---|---|---|---|---|---|---|---|---|
| 774.3 | 2.89 | 10 | \|10\|0\|0\|0\|0\|0\|0\| | 10 | 100 | 6.96 | 6.73 | 6.73 | 0.000813 |
| 658.2 | 2.82 | 10 | \|0\|7\|0\|0\|0\|0\|0\| | 7 | 70 | 5.52 | 5.77 | 5.77 | 0.000416 |
| 559 4 | 2.75 | 10 | \|0\|4\|0\|0\|0\|0\|0\| | 4 | 40 | 4.75 | 4.82 | 4.82 | 0.000015 |
| 475.5 | 2.68 | 10 | \|0\|2\|0\|0\|0\|0\|0\| | 2 | 20 | 4.16 | 3.86 | 3.86 | −0.000378 |
| 404.2 | 2.61 | 10 | \|0\|0\|0\|0\|0\|0\|0\| | 0 | 0 | 3.04 | 2.91 | 2.91 | −0.000774 |

Example 11 Acute Toxicity of Levamlodipine Besylate Hydrate Composition Tablets In this experiment the tablet formulation is the one of Example 5, in which the crystalline water content of the levamlodipine besylate hydrate composition is 5.3%.

In this experiment, the LD50 is measured by two administration routes. Oral administration and intraperitoneal administration of levamlodipine besylate hydrate composition tablets, grinding the tablets into uniform fine powder, and then using 10% gum Arabic to prepare two groups of liquid mixtures at a suitable concentration for oral administration and intraperitoneal administration. Animals: Kunming mice, half male and half male, each weighing 18-28 g, Significance index G=0.2002 X50=2.7612 SX=0.0172 G is relatively small and has been omitted.

Heterogeneity check Ch2=1.51 Ch2.05=7.82 Sb=3.3.0947 No heterogeneity.

Converted into the levamlodipine besylate hydrate composition (calculated in levamlodipine) is LD50=16.0212±1.3774 mg/kg.

Example 12 Pharmacokinetics of Sustained-Release Formulation

Please see Example 8 for the drug formulation of the fast-sustained-release formulation of the levamlodipine besylate hydrate composition used in this experiment. The purpose of this experiment is to study the pharmacokinetic behavior of the sustained-release tablets of the levamlodipine besylate hydrate composition (test preparation, dosage 10 mg/tablet,) in Beagle dogs, and to investigate whether it has the pharmacokinetic characteristic of fast and sustained dual release. The relative bioavailability in Beagle dogs is evaluated by using the solution of levamlodipine besylate hydrate composition prepared by the method described in Example 1 of the present invention as a reference preparation. Five adult and healthy Beagle dogs, all male, are divided into two groups for a single-dose administration experiment. The test and reference preparations are orally administered to the Beagle dogs on an empty stomach at a dose of 10 mg/dog, and plasma samples are collected at different time points. Liquid chromatography-mass spectrometer is used to determine the concentration of the levamlodipine besylate hydrate composition (calculated in levamlodipine) in plasma, and the pharmacokinetic parameters are calculated. The following results are obtained:

TABLE 13

Pharmacokinetic Parameters After Single-Dose Oral Administration of Test and Reference Preparations of Levamlodipine Besylate Hydrate Composition (mean ± SD)

| Pharmacokitetic Parameter | Test Preparation | Reference Preparation |
|---|---|---|
| $T_{max}$(h) | 7.3 ± 1.2 | 2.0 ± 0.0 |
| $C_{max}$(ng/ml) | 47.4 ± 7.5 | 69.8 ± 19.7 |
| $AUC_{0-t}$(ng · h/ml) | 1035.3 ± 318.5 | 1204.0 ± 415.8 |
| $AUC_{0-\infty}$(ng · h/ml) | 1131.0 ± 385.4 | 1281.0 ± 492.1 |
| $MRT_{(h)}$ | 19.3 ± 4.5 | 16.4 ± 3.5 |
| $t_{1/2}$(h) | 12.3 ± 2.8 | 11.2 ± 2.8 |
| F (%) | | 86.0% |

Figure 10:
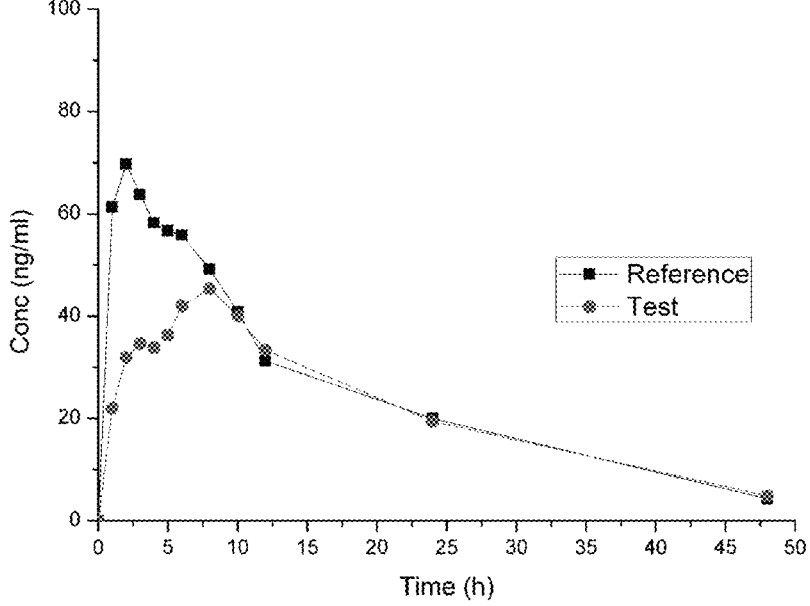
FIG. 10: a mean plasma concentration-time curve of beagles after oral administration of 10 mg of a test preparation of a levamlodipine besylate hydrate composition and a reference preparation.

After oral administration of 10 mg of the test and reference preparations of the levamlodipine besylate hydrate compositions to Beagle dogs, the mean plasma concentration-time curve is shown in FIG. 10.

The results show that after oral administration of the sustained-release tablets of the levamlodipine besylate hydrate compositions to Beagle dogs, the average peak plasma concentration of levamlodipine in the dogs is 47.4 ng/ml, which is lower than the peak concentration of 69.8 ng/ml of the reference preparation by 32%, indicating that the sustained-release tablets can effectively reduce the peak concentration of the fast-release preparation; The plasma concentration of the sustained-release tablets of the levamlodipine besylate hydrate 1 hour after administration is more than 20% of the peak concentration of the reference preparation, and the average peak time is 7.3 h, which is longer than the 2.0 h peak time of the reference preparation. It has the fast and sustained dual release characteristic, and can maintain a steady plasma concentration over a period of time; the bioavailability of the sustained-release tablets of the levamlodipine besylate hydrate composition relative to the reference preparation is 86.0%, indicating that the absorption degree of the two preparations in Beagle dogs is basically the same. Given that the gastrointestinal tract of dogs is relatively short and the drug excretion is relatively fast, it is expected that the sustained release effect and the degree of absorption of the sustained-release preparation in human trials will be better than those of dogs.

The invention claimed is:

1. A fast-sustained-release tablet formulation comprising a sustained-release layer and a fast-release layer, each of which comprises levamlodipine besylate hydrate compounds having different crystalline water content, wherein the levamlodipine besylate hydrate has a molecular formula of $C_{20}H_{25}ClN_2O_5 \cdot C_6H_6O_3S \cdot nH_2O$, wherein 1<n<2, and has the following structural formula:

wherein the levamlodipine besylate hydrate comprises 4.5%-5.8% of crystalline water, wherein the sustained-release layer comprises levamlodipine, polyvinylpyrrolidone, hydroxypropyl cellulose, microcrystalline cellulose, and magnesium stearate in a mass ratio of 4-5:30-40:55-65:17-30:0.1-1, and wherein the fast-release layer comprises levamlodipine, microcrystalline cellulose, pregelatinized starch, cross-linked polyvinylpyrrolidone, polyvinylpyrrolidone, and magnesium stearate in a mass ratio of 1-2:40-45:35-45:1-8:5-15:0.1-1.

2. The fast-sustained-release tablet formulation of claim 1, wherein the levamlodipine besylate hydrate comprises 4.5%-5.5% of crystalline water.

3. The fast-sustained-release tablet formulation of claim 1, wherein the levamlodipine besylate hydrate comprises 4.5%-5.4% of crystalline water.

4. A fast-sustained-release combination tablet comprising a sustained-release combination layer and a fast-release combination layer, each of which comprises levamlodipine besylate hydrate compounds having different crystalline water content, wherein the levamlodipine besylate hydrate has a molecular formula of $C_{20}H_{25}ClN_2O_5 \cdot C_6H_6O_3S \cdot nH_2O$, wherein 1<n<2, and has the following structural formula:

wherein the levamlodipine besylate hydrate comprises 4.5%-5.8% of crystalline water, wherein the sustained-release combination layer comprises levamlodipine, polyvinylpyrrolidone, hydroxypropyl cellulose, microcrystalline cellulose, and magnesium stearate in a mass ratio of 4-5:30-40:55-65:17-30:0.1-1, and wherein the fast-release combination layer comprises levamlodipine, folic acid, microcrystalline cellulose, pregelatinized starch, cross-linked polyvinylpyrrolidone, polyvinylpyrrolidone, and magnesium stearate in a mass ratio of 1-2:0.1-1:40-45:35-45:1-8:5-15:0.1-1.

5. The fast-sustained-release combination tablet of claim 4, wherein the sustained-release combination layer comprises levamlodipine, polyvinylpyrrolidone, hydroxypropyl cellulose, microcrystalline cellulose, and magnesium stearate in a mass ratio of 4.5:35:60:23.9:0.5, and wherein the fast-release combination layer comprises levamlodipine, folic acid, microcrystalline cellulose, pregelatinized starch, cross-linked polyvinylpyrrolidone, polyvinylpyrrolidone, and magnesium stearate in a mass ratio of 1.5:0.4:40.5:40:5:10:0.5.

6. A composition comprising levamlodipine besylate hydrate compounds having different crystalline water content, wherein the levamlodipine besylate hydrate has a molecular formula of $C_{20}H_{25}ClN_2O_5 \cdot C_6H_6O_3S \cdot nH_2O$, wherein n is within the range of 1.83 to 1.94, and has the following structural formula:

and wherein the levamlodipine besylate hydrate comprises 4.5%-5.8% of crystalline water.

7. The composition of claim 6, wherein n is 1.83 or 1.94.

* * * * *